US008195534B2

(12) United States Patent
Frankel

(10) Patent No.: US 8,195,534 B2
(45) Date of Patent: Jun. 5, 2012

(54) METHOD AND SYSTEM FOR PREPARING A SET OF PAIRED IDENTIFICATION LABELS

(75) Inventor: Mark E. Frankel, Lower Gwynedd, PA (US)

(73) Assignee: Quiq, Inc., Blue Bell, PA (US)

(*) Notice: Subject to any disclaimer, the term of this patent is extended or adjusted under 35 U.S.C. 154(b) by 0 days.

(21) Appl. No.: 13/070,716

(22) Filed: Mar. 24, 2011

(65) Prior Publication Data

US 2011/0226412 A1  Sep. 22, 2011

Related U.S. Application Data

(60) Division of application No. 12/197,398, filed on Aug. 25, 2008, now Pat. No. 7,930,222, which is a continuation-in-part of application No. 11/894,768, filed on Aug. 21, 2007, now Pat. No. 7,860,605, which is a continuation-in-part of application No. 11/476,220, filed on Jun. 27, 2006, now Pat. No. 7,483,766, which is a continuation-in-part of application No. 11/820,564, filed on Jun. 21, 2007, now Pat. No. 7,912,578.

(51) Int. Cl.
*G06Q 10/00* (2012.01)
*G09F 3/00* (2006.01)
*G09C 3/00* (2006.01)

(52) U.S. Cl. ............... 705/28; 40/310; 283/81

(58) Field of Classification Search .................. None
See application file for complete search history.

(56) References Cited

U.S. PATENT DOCUMENTS

| | | | |
|---|---|---|---|
| 4,767,917 | A | 8/1988 | Ushikubo |
| 4,812,629 | A | 3/1989 | O'Neil et al. |
| 4,847,764 | A | 7/1989 | Halvorson |
| 5,014,875 | A | 5/1991 | McLaughlin et al. |
| 5,431,299 | A | 7/1995 | Brewer et al. |
| 5,797,515 | A | 8/1998 | Liff et al. |
| 5,883,370 | A | 3/1999 | Walker et al. |
| 6,032,155 | A | 2/2000 | de la Huerga |
| 6,067,524 | A | 5/2000 | Byerly et al. |
| 6,109,774 | A | 8/2000 | Holmes et al. |
| 6,219,587 | B1 | 4/2001 | Ahlin et al. |
| 6,330,491 | B1 | 12/2001 | Lion |
| 6,352,200 | B1 | 3/2002 | Schoonen et al. |
| 6,529,801 | B1 | 3/2003 | Rosenblum |
| 6,564,121 | B1 | 5/2003 | Wallace et al. |
| 6,636,780 | B1 | 10/2003 | Haitin et al. |
| 6,766,218 | B2 | 7/2004 | Rosenblum |
| 6,769,228 | B1 | 8/2004 | Mahar |
| 6,860,513 | B2 * | 3/2005 | Kaufman ................ 283/81 |
| 6,892,941 | B2 | 5/2005 | Rosenblum |
| 6,985,870 | B2 | 1/2006 | Martucci et al. |
| 7,123,989 | B2 | 10/2006 | Pinney et al. |
| 7,194,333 | B2 | 3/2007 | Shoenfeld |

(Continued)

*Primary Examiner* — Paul Danneman
(74) *Attorney, Agent, or Firm* — Howard IP Law Group, PC

(57) ABSTRACT

A system and method for preparing a set of paired identification label based a plurality of characters that identify an inventory item. The method includes a step of assigning a predetermined numerical value to each of the plurality of characters. Mathematical operations are performed on the assigned numerical values to obtain a mapping of the plurality of characters to a corresponding non-textual visual indicator. A label is generated which label includes the plurality of characters and the visual indicator. The visual indicator may be a color or a graphic indicator such as an alignment designation bar or a combination and variation thereof.

11 Claims, 17 Drawing Sheets

U.S. PATENT DOCUMENTS

| | | |
|---|---|---|
| 7,483,766 B1 | 1/2009 | Frankel |
| 2002/0062175 A1 | 5/2002 | Lion |
| 2003/0050731 A1 | 3/2003 | Rosenblum |
| 2003/0074218 A1 | 4/2003 | Liff et al. |
| 2004/0215369 A1 | 10/2004 | Rosenblum |
| 2005/0049746 A1 | 3/2005 | Rosenblum |
| 2005/0075908 A1 | 4/2005 | Stevens |
| 2005/0166144 A1* | 7/2005 | Gross .................. 715/526 |
| 2005/0281601 A1 | 12/2005 | Papetti |

* cited by examiner

300

| 0 | 250 |
|---|---|
| 1 | 25 |
| 2 | 50 |
| 3 | 75 |
| 4 | 100 |
| 5 | 125 |
| 6 | 150 |
| 7 | 175 |
| 8 | 200 |
| 9 | 225 |

FIG. 4

| | | | | | | | | | | | | | 420 | 410 |
|---|---|---|---|---|---|---|---|---|---|---|---|---|---|---|
| Row $120_1$ | 11 | 30 | 15 | 24 | 25 | 22 | 23 | 24 | 0 | 0 | 0 | 0 | 174 | Row 1 Total |
| Row $120_2$ | 0 | 0 | 3 | 6 | 23 | 17 | 0 | 0 | 0 | 0 | 0 | 0 | 49 | Row 2 Total |
| Row $120_3$ | 0 | 0 | 6 | 0 | 23 | 17 | 0 | 0 | 0 | 0 | 0 | 0 | 51 | Row 3 Total |
| Row $120_4$ | 2 | 1 | 1 | 0 | 13 | 25 | 31 | 24 | 30 | 0 | 0 | 0 | 126 | Row 4 Total |

| Row 1 Total | 174 | × 1 = | 174 | "A" |
|---|---|---|---|---|
| Row 2 Total | 49 | × 2 = | 98 | "B" |
| Row 3 Total | 51 | × 3 = | 153 | "C" |
| Row 4 Total | 126 | × 4 = | 504 | "D" |

FIG. 6

| RGB Colors | PMS Colors |
|---|---|
| (100,25,0) | 4995C |
| (0,225,0) | 345C |
| (60,0,150) | 272C |
| (255,255,100) | 100C |
| (255,50,255) | 245C |
| (50,100,175) | 284C |

2300

| | |
|---|---|
| 0 | 47 |
| 1 | 7 |
| 2 | 11 |
| 3 | 13 |
| 4 | 17 |
| 5 | 19 |
| 6 | 23 |
| 7 | 29 |
| 8 | 31 |
| 9 | 37 |
| a | 43 |
| b | 47 |
| c | 53 |
| d | 59 |
| e | 61 |
| f | 67 |
| g | 71 |
| h | 73 |
| i | 79 |
| j | 83 |
| k | 89 |
| l | 97 |
| m | 101 |

| | |
|---|---|
| n | 103 |
| o | 107 |
| p | 109 |
| q | 113 |
| r | 127 |
| s | 131 |
| t | 137 |
| u | 139 |
| v | 149 |
| w | 151 |
| x | 157 |
| y | 163 |
| z | 167 |

FIG. 23

METHOD AND SYSTEM FOR PREPARING A SET OF PAIRED IDENTIFICATION LABELS

CROSS-REFERENCE TO RELATED APPLICATIONS

This application is a divisional application of U.S. patent application Ser. No. 12/197,398 filed on Aug. 25, 2008, entitled the same, which is a continuation-in-part of and claims priority of U.S. patent application Ser. No. 11/894,768, entitled A SYSTEM FOR CONTROLLING ACCESS TO AND SEGREGATING DISPENSED ITEMS, filed Aug. 21, 2007, which is a continuation-in-part of U.S. patent application Ser. No. 11/476,220, filed Jun. 27, 2006, and U.S. patent application Ser. No. 11/820,564, filed Jun. 21, 2007, the entire disclosures of which are hereby incorporated herein by reference in their entireties.

FIELD OF THE INVENTION

The present invention relates generally to a method and a system for preparing a set of paired identification labels.

BACKGROUND OF THE INVENTION

Some inventory items that are delivered to a location need to be associated with paper records and/or forms. Bar code scanning, RFID labeling and other such technological solutions require equipment to be present at the location of delivery. The costs of providing this equipment in the field may be prohibitive due to the harsh environment such as shop floors, the economics of the area (e.g., third-world countries) or the skill sets of the individuals who are responsible for delivering such items. Sometimes, in case of prescription drugs, pre-packaged units of medications may be kept in a bulk inventory setting and then selected by a technician for delivery to patients or related individuals. The patient information sheets and prescriptions need to be associated with a particular pre-packaged unit of medication. Errors in this association may have grave results to the health of the individual, as evidenced by the large numbers of deaths in this country per year due to a wrong drug reaching a patient.

Current methods for matching rely on oversight by a trained professional to check the package and labeling on the drug unit and the prescription given to a patient; however, this is still susceptible to human error.

SUMMARY OF THE INVENTION

An embodiment of the invention includes a method for generating an identification label based on a plurality of characters that identify an inventory item. The method includes a step of assigning a predetermined numerical value to each of the plurality of characters, wherein each unique character is assigned a corresponding unique numerical value or number. The method includes a further step of performing mathematical operations on the assigned numerical values to obtain a mapping of the plurality of characters to a corresponding non-textual visual indicator. The method further includes a step of generating the label which includes the plurality of characters and the visual indicator.

Another embodiment of the invention includes a method for matching a deliverable unit with an information sheet using a set of paired identification labels. The method includes a step of affixing a set of identification labels based on a plurality of characters which are indicative of the content of the deliverable unit, wherein the set is generated based on the plurality of characters. The set of identification labels includes a first label in a first color and having the plurality of characters printed thereon. The first label has a first visual indicator printed adjacent to at least one edge of the first label. The set also includes a second label which is identical to the first label and is removably superimposed on the first label. The method further includes a step of generating an information sheet. The information sheet further includes a label image and a blank space adjacent to the label image. The label image is printed in the first color and has a third visual indicator printed adjacent to at least one edge of the label image. The method also includes the steps of removing the second label from the deliverable unit and affixing the second label in the blank space adjacent to the label image. The second label and the label image are printed in the first color, and have the same plurality of characters printed thereon. The second and third visual indicators align or match with each other at the adjacent edges of the second label and the label image only when the plurality of the characters on the information sheet and the deliverable unit match, wherein the plurality of characters are indicative of a content to be delivered to a bearer of the information sheet.

A further embodiment of the invention is a set of paired identification labels including a first label having a plurality of characters printed thereon and a second label having the plurality of characters printed thereon. A first alignment designation bar is printed across the first label and a second alignment designation bar is printed across the second label. When the first and second labels are located adjacent to each other, the first and the second alignment designation bars align with each other at the edges of the first and the second labels. The first and second labels may be printed in a first color. In another embodiment, the first alignment designation bar divides the first label into first and second parts and the second alignment designation bar divides the second label into third and fourth parts. The first and third parts of the set may be printed in a first color and the second and the fourth parts of the set may be printed in a second color.

BRIEF DESCRIPTION OF THE FIGURES

Understanding of the present invention will be facilitated by consideration of the following detailed description of the exemplary embodiments of the present invention taken in conjunction with the accompanying drawings, in which like numerals refer to like parts and in which:

FIG. 4 shows an exemplary color look up table 300;

FIG. 5 illustrates an assignment of a numerical value to each character in an exemplary label and calculation of row total for each row of characters in the exemplary label 100;

FIG. 6 illustrates an exemplary calculation of values of variables "A," "B," "C," and "D" based on the row totals for label 100;

FIG. 23 illustrates another exemplary character lookup table.

DETAILED DESCRIPTION OF THE INVENTION

It is to be understood that the figures and descriptions of the present invention have been simplified to illustrate elements that are relevant for a clear understanding of the present invention, while eliminating, for purposes of clarity, many other elements found in typical labeling systems. However, because such elements are well known in the art, and because they do not facilitate a better understanding of the present invention, a discussion of such elements is not provided herein. The disclosure herein is directed to all such variations and modifications known to those skilled in the art.

A challenge identified by the inventor is a need for a method and system which creates a quick and readily apparent check to insure that the correct prescription is given to the correct patient. Such checks are particularly important when considering scheduled pharmaceuticals as any item that is taken out of inventory control loses its attachment to the responsible individual. The present invention is based on a general idea of mapping a unique visual indicator from a given set of characters, such that a difference in a single character in the set would result in a different visual indicator. The attributes of the visual indicator are, thus, based on and uniquely mapped to a given set of characters.

Figure 1:
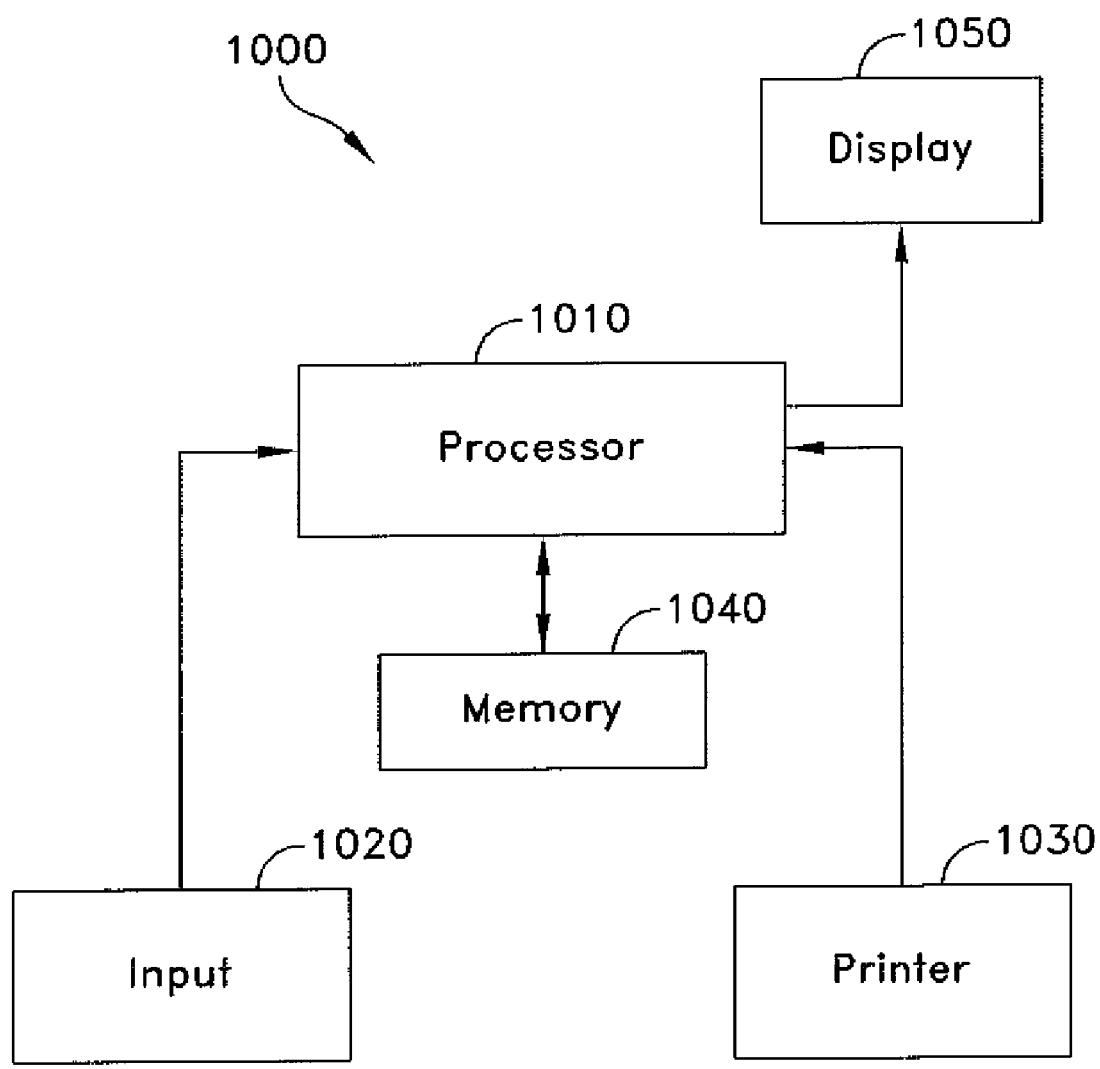
FIG. 1 illustrates a schematic diagram of an exemplary system for generating a set of paired identification labels.

Referring to FIG. 1, a system 1000 is illustrated schematically. System 1000 includes a processor 1010, a memory 1040 accessible to processor 1010, a display 1050, an input 1020, and a printer 1030. "Processor" as used herein, generally refers to a circuit arrangement that may be contained on one or more silicon chips, and/or integrated circuit (IC) boards, and that contains a Central Processing Unit (CPU). The CPU may generally include an arithmetic logic unit (ALU), which performs arithmetic and logical operations, and a control unit, which extracts instructions from memory and decodes and executes them, calling on the ALU when necessary.

Processor 1010 may take form of a microprocessor, by way of non-limiting example only. The present invention is operable with computer storage products or computer readable media that contain computer program code for performing the various computer-implemented operations. The computer readable medium is any data storage device that can store data which can thereafter be read by a computer system such as a microprocessor. The media and program code may be those specially designed and constructed for the purposes of the present invention, or they may be of the kind well known to those of ordinary skill in the computer software arts. Examples of computer readable media include, but are not limited to magnetic media such as hard disks, floppy disks, and magnetic tape; optical media such as CD-ROM disks; magneto-optical media; and specially configured hardware devices such as application-specific integrated circuits (ASICs), programmable logic devices (PLDs), and ROM and RAM devices. Examples of program code include both machine code, as produced, for example, by a compiler, or files containing higher-level code that may be executed using an interpreter.

Memory 1040 may include data storage and retrieval devices including internal and external devices including volatile and non-volatile memory, Read-only Memory (ROM), Random Access Memory (RAM), cache, hard disks, floppy diskettes, magnetic tapes, optical discs such as compact discs (CD), digital versatile discs (DVD), memory sticks and thumb drives. By way of example, input 1020 may include keyboards, touch screen input devices, optical disc readers, and optical scanners. Printer 1030 may include inkjet printers, and laser printers, for example. Display 1050 may include, by way of example, a monitor. As such components as processor, display, memory, input and printers are known in the art, they are not described in further detail.

Figures 2, 3:
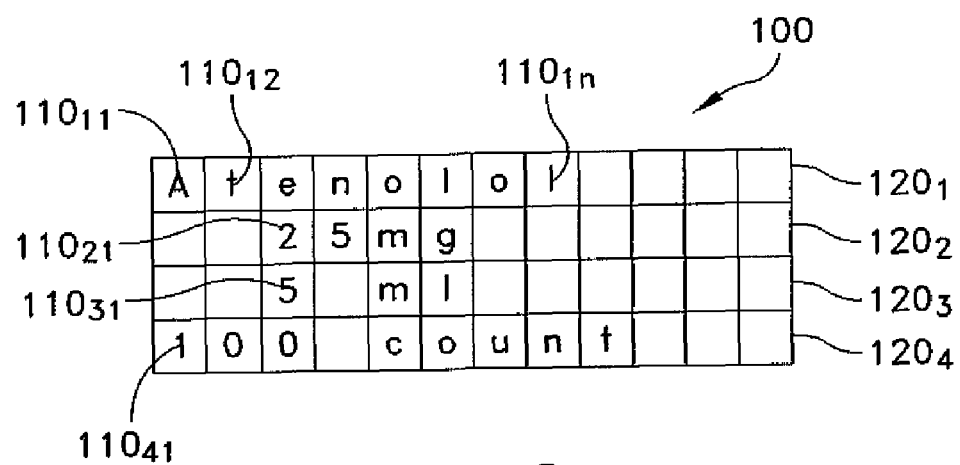
FIG. 2 illustrates an exemplary text for a label 100.
FIG. 3 illustrates an exemplary character look up table 200.

Now referring to FIG. 2, an exemplary label or label image 100 is illustrated. Terms "label" and "label image" may be used interchangeably and both the terms indicate a text-box containing at least a plurality of characters and one or more visual indicators. Label 100 is a generally flexible, planar substrate with information printed thereupon and may have a layer of adhesive applied to a surface to be affixed to a deliverable unit or other surface. Label 100 is representative of the information to be printed on the set of paired identification labels (610 of FIG. 7) to be generated by system 1000 (of FIG. 1). The information on label 100 may be fed to system 1000 via input means 1020. Label 100 has a plurality of characters $110_{11}, 110_{12} \ldots 110_{1n}$ in a row $120_1$ printed thereupon. In an exemplary embodiment, label 100 has four rows $120_1, 120_2, 120_3,$ and $120_4$, each having a plurality of characters ($110_{11}, 110_{12} \ldots 110_{1n}$); ($110_{21}, 110_{22} \ldots 110_{2n}$) ... ($110_{41}, 110_{42} \ldots 110_{4n}$) respectively. In this illustrated embodiment, the label information area is divided into cells, each cell containing one character. It is understood that labels may be of different sizes (e.g. different lengths and widths) according to different applications, however, each cell in the matrix of rows and columns may be configured so that the characters can be read in or out in uniform fashion by a corresponding read/write engine.

Referring now to FIG. 3, an exemplary character look up table 200 is illustrated. A unique numerical value is associated with each character in look up table 200. In the exemplary character look up table 200 illustrated here, each digit 0-9 is assigned a numerical value ranging from 1-10 and each character a-z is assigned a numerical value ranging from 11-35. In another embodiment, other special characters may also be assigned a unique numerical value. For example, another exemplary character look up table 2300 is illustrated in FIG. 23. Again, a unique numerical value is associated with each character. In the exemplary character look up table 2300 illustrated here, each digit 0-9 is assigned a unique prime number ranging from 7-37 for digits 1-9 and 41 for digit 0. Each character a-z is assigned a prime number ranging from 43-167. Digit zero (0) is assigned a sizable prime number (41) because zero (0) is a common character likely to frequently appear on a label associated with a dispensed pharmaceutical, for example, in dosage and count fields.

In yet another embodiment, each of lower case and upper case letters of the alphabet may be assigned a unique numerical value. Look up table 200 may be stored in memory 1040 (of FIG. 1) or may otherwise be accessible to processor 1010 (of FIG. 1) via computer storage products or computer readable media.

Now referring to FIG. 4, an exemplary color look up table 300 is illustrated. In an exemplary embodiment, each digit 0-9 is assigned a numerical value ranging from 25-250. In another embodiment, digits 0-9 may be assigned different numerical values also. Look up table 300 may also be stored in memory 1040 (of FIG. 1) or be otherwise accessible to processor 1010 (of FIG. 1) via computer storage products or computer readable media.

Now referring to FIGS. 2, 3 and 5, each character $110_n$ in each row $120_n$ is assigned a numerical value based on character look up table 200. In an exemplary embodiment, a row total is calculated for each row $120_n$, as shown in FIG. 5 by adding the numerical values for each character in a row $120_n$. This may be accomplished using a processor in conjunction with a read/write engine. For exemplary label 100, the row totals 410, 420, 430, and 440 are 174, 49, 51, and 126 for the first, second, third and fourth rows $120_1$, $120_2$, $120_3$, and $120_4$ respectively. Row totals may be calculated using a computer program, for example, a spreadsheet program available from Microsoft Corporation as MS Excel®, and stored in memory 1040, for example, for later retrieval. In other embodiments, different algorithms may be used to calculate row totals, for example, calculating a subtotal by summing up numerical values for each alternate character in a row and calculating another subtotal by summing up numerical values for the other characters in the same row and multiplying one subtotal by two and adding it to the first subtotal.

Referring now to FIG. 6, in an exemplary embodiment, four variables A, B, C, and D are defined using the row totals calculated in FIG. 5 and stored in memory 1040, for example. In other embodiments, variables may be less than or more than four. Various approaches are possible for calculating these variables. In one exemplary embodiment, $A$=Row 1 Total×1;

$B$=Row 2 Total×2;

$C$=Row 3 Total×3; and $D$=Row 4 Total×4.

Other methods may also be utilized, for example, assigning the values of the row totals to variables A, B, C, and D or using different multiple values, as shown below:

| | | | |
|---|---|---|---|
| A = | Row 1 Total | A = | Row 1 Total × 4 |
| B = | Row 2 Total | B = | Row 2 Total × 3 |
| C = | Row 3 Total; and | C = | Row 3 Total × 2; and |
| D = | Row 4 Total. | D = | Row 4 Total × 1. |

Thus, a variety of other mathematical operations, for example, addition or subtraction, may also be performed on the row totals for generating values for these four variables. Variables A, B, C and D may be calculated using a computer program, for example, a spreadsheet program available from Microsoft Corporation as MS Excel®. For exemplary label 100, the values of A, B, C, and D are 174, 98, 153, and 504 respectively using the first exemplary method. In yet another embodiment, variables A, B, C, and D may be calculated by selectively performing mathematical operations on the numerical values for each character on label 100. For example, variable A may be calculated by summing the numerical values assigned to first, fifth, ninth, . . . character; variable B may be calculated by summing the numerical values assigned to second, sixth, tenth, . . . character; variable C may be calculated by summing the numerical values assigned to third, seventh, eleventh, . . . characters; and variable D may be calculated by summing the numerical values assigned to fourth, eighth, twelfth, . . . characters on label 100. Other algorithms and other mathematical operations may also be applied to calculate the values of four variables A, B, C, and D.

As is known in the art, a color model is an abstract mathematical model describing the way colors can be represented as a tuple or a set of numbers, typically as three or four values or color components. In an exemplary embodiment, the RGB color model is utilized, wherein various values of three primary colors Red (R), Green (G) and Blue (B) are used to define a particular color. Other color models such as HSV (Hue, Saturation, and Value), HSL (Hue, Saturation, and Lightness), or CMYK (Cyan, Magenta, Yellow and Key (black)) may also be used. In an exemplary embodiment, the color model is represented as a tuple of three numbers, one each for Red, Green and Blue. In another embodiment, a tuple may have more or less than three components, for example, a tuple of four numbers, one each for Cyan, Magenta, Yellow and Key (Black).

In an exemplary embodiment, the values for each of the components, R, G, and B are derived from different combinations of at least two of the variables A, B, C and D. Similar approach may be used to derive the values for each the C, M, Y, and K component. In an exemplary embodiment, R is assigned a numerical value from the color look up table of FIG. 3, wherein the numerical value corresponds to the last digit of the sum of A and B;

G is assigned a numerical value from the color look up table of FIG. 3, wherein the numerical value corresponds to the last digit of the sum of A and C;

B is assigned a numerical value from the color look up table of FIG. 3, wherein the numerical value corresponds to the last digit of the sum of A and D.

In another embodiment, another mathematical operation, for example, subtraction or multiplication may be performed on at least two variables for deriving the values of R, G and B. Values of color components R, G, and B may be calculated using a computer program, for example, a spreadsheet program available from Microsoft Corporation as MS Excel®. For the exemplary label 100, $$A+B=174+98=272$$

$$A+C=174+153=327$$

$$A+D=174+504=678$$

For exemplary label 100, the values of R, G, and B are respectively 50 (based on the value corresponding to the last digit 2 of the sum (A+B) in the color look up table of FIG. 3), 175 (based on the value corresponding to the last digit 7 of the sum (A+C) in the color look up table of FIG. 3), and 200 (based on the value corresponding to the last digit 8 of the sum (A+D) in the color look up table of FIG. 3). Thus, the color of each of the pair of identical labels generated will be defined by the tuple (50, 175, 200).

In a similar fashion, the x-coordinates and the y coordinates of alignment designation bar 630 (of FIG. 7) are also derived from the variables A, B, C, and D. In an exemplary embodiment, the y-coordinate of the beginning point of bar 630 (of FIG. 7) is 0 and the y-coordinate of the end point of bar 630 (of FIG. 7) is 20. In an exemplary embodiment, the x-coordinate of the beginning point of bar 630 (of FIG. 7) is the last digit 1 of the sum (B+C=251) and the x-coordinate of the end point of bar 630 (of FIG. 7) is the last digit 2 of the sum (B+D=602). It is to be understood that other variables may also be used to derive the value of the x-coordinates of the beginning point and the end point of bar 630 (of FIG. 7). The x-coordinates and the y-coordinates of bar 630 (of FIG. 7) may be calculated using a computer program, for example, a spreadsheet program available from Microsoft Corporation as MS Excel®. For exemplary label 100, the beginning point of bar 630 (of FIG. 7) is (1, 0) and the end point of bar 630 (of FIG. 7) is (2, 20).

In another exemplary embodiment, using the character look up table of FIG. 23, the x-coordinate and the y-coordinate may be calculated as follows.

$$A=\text{Row 1 Total}$$

$$B=\text{Row 2 Total}$$

$$C=\text{Row 3 Total}$$

$$D=\text{Row 4 Total}$$

$x=A+(B*107)+(C*15)+(D*101)$, wherein all the digits of the calculated total are summed up; and $y=A+(B*7)+(C*431)+(D*11)$, wherein all the digits of the calculated total are summed up.

If the sum of the total is less than or equal to 19, the sum may be used as the coordinate. If the sum of the total is in the range 20-25, 0 is used as the coordinate. If sum of the total is greater than 25, all the digits are again added to get the coordinate. Thus, in this exemplary embodiment, operators are applied on all four variables to derive the x-coordinate and the y-coordinate, which values will change if there is a change in the characters in any row of label 100.

Figure 16:
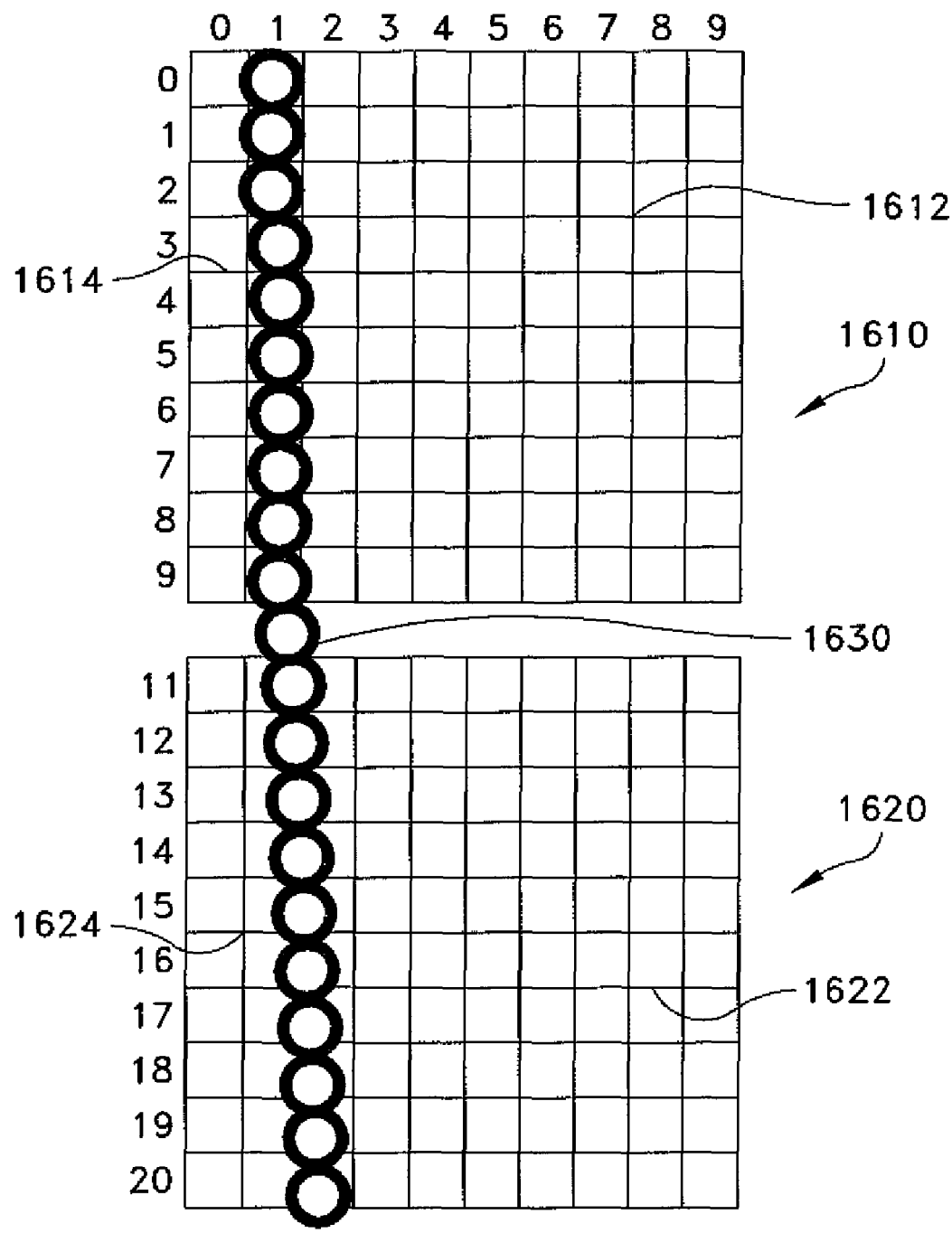
FIG. 16 illustrates another exemplary set of paired identification labels corresponding to label 100 with an different type of alignment designation bar.
Figure 17:
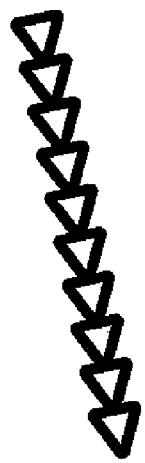
FIG. 17 illustrates yet another embodiment of an alignment designation bar.
Figure 18A:
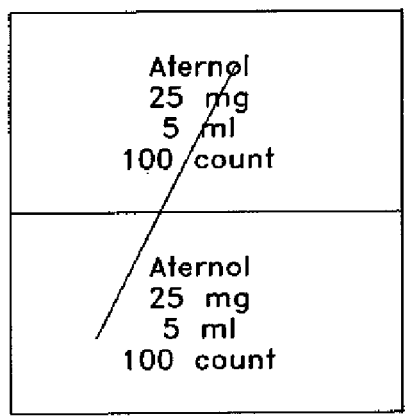
FIGS. 18A-18D illustrate other embodiments of an alignment designation bars.
Figure 18B:
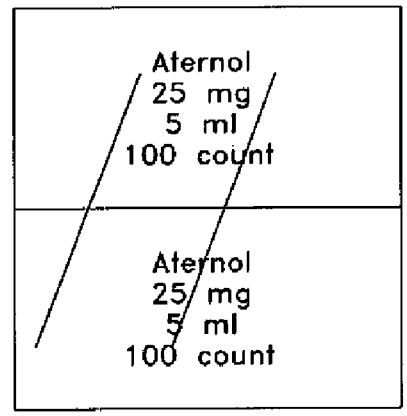
Figure 18C:
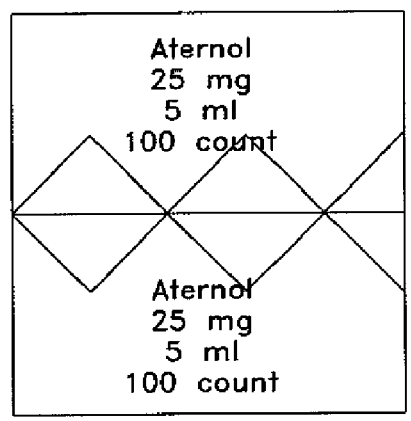
Figure 18D:
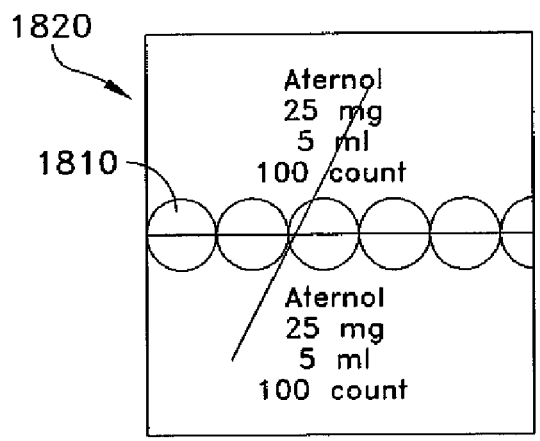

In another embodiment, a visual indicator may include a visual pattern such as two alignment bars, or a hatch pattern or a non-linear bar may also be used. The terms "alignment designation bar" and "visual indicators" are used interchangeably and they include other such visual patterns as well. Such an alignment designation bar may be aligned by location and may also be aligned by orientation at adjacent edges of the pair of identical labels. In one embodiment, an alignment designation bar may be a series of symbols such as circles or triangles having a starting point and an end point as determined by the method described above. Thus, an alignment designation bar is not limited to a straight line but also includes other shapes and forms, for example, as shown in FIGS. 16 and 17, that assist in verifying a match between two labels and have a starting point and an end point calculated from variables A, B, C and D.

Other embodiments of alignment designation bars or visual indicators are illustrated in FIGS. 18A-18D. Such alignment designation bars may be generated based on the plurality of characters printed on label 100. For example, the diameter of circles 1810 may be generated by performing mathematical operations on the plurality of characters printed on label set 1820. Since one skilled in the art may recognize that various algorithms or mathematical operations may be performed on a given set of characters to calculate the diameter of circles or the slope of the lines, such algorithms or mathematical operations are not described in detail for the sake of brevity.

Figure 7:
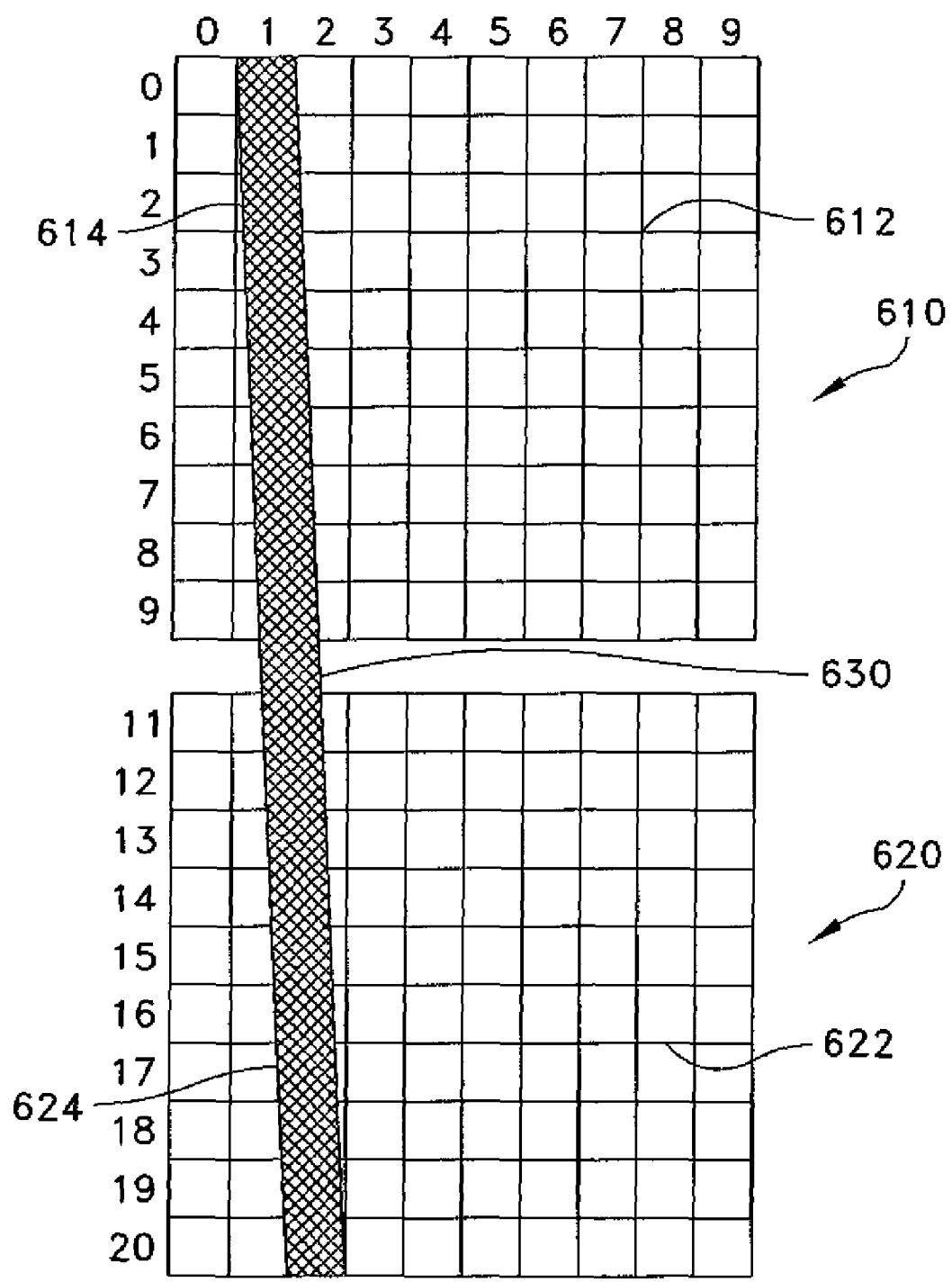
FIG. 7 illustrates an exemplary set of paired identification labels with an alignment designation bar.

FIG. 7 illustrates an exemplary set of paired identification labels 610 and 620. In the illustrated embodiment, two labels 610, 620 are paired with each other. In another embodiment, a plurality of labels may be combinedly paired with at least one other label or label image. The term "paired" is not intended to limit the number of labels to two; rather, it is intended to include any number of labels matched and/or aligned combinedly with at least one other label or label image. Alignment designation bar 630 is printed across labels 610, 620. Label 610 has two distinct areas 612 and 614 separated by bar 630. Likewise, label 620 has two distinct areas 622 and 624 separated by bar 630. The exemplary set of paired identification labels 610 and 620 are based on exemplary label 100 and have a color defined by RGB (50, 250, 200).

Figure 8:
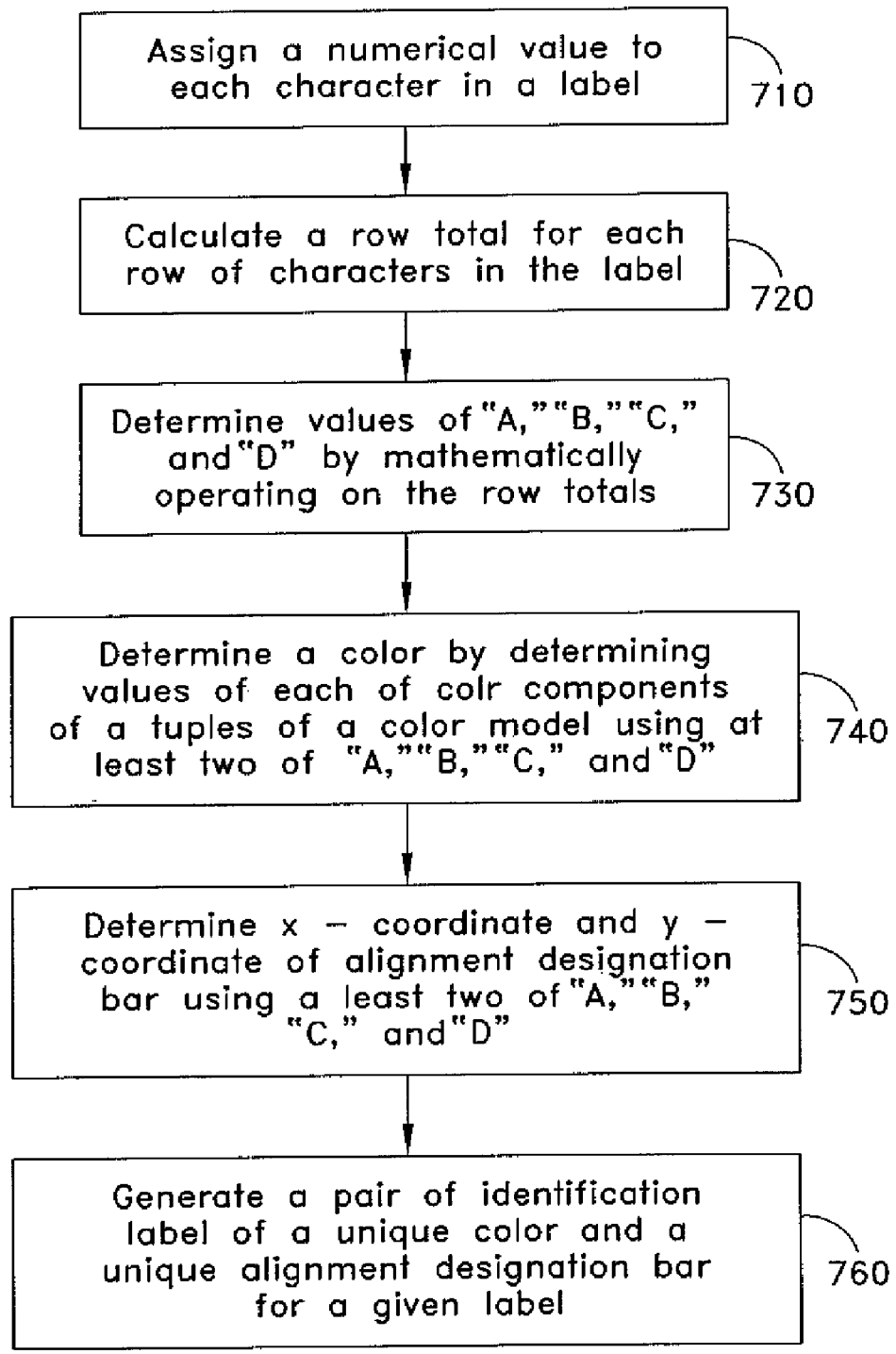
FIG. 8 illustrates a flow chart for generating a paired identification label for a given label of FIG. 1 using a character look up table of FIG. 2 and a color look up table of FIG. 3.

Now referring to FIG. 8, a flow chart of the process of preparing a set of paired identification labels according to an embodiment of the invention will be described. At block 710, a numerical value is assigned to each character on a label. A row total is calculated for each row of characters in the label, at block 720. Mathematical operations are performed on the calculated row totals to derive the values of the variables A, B, C, and D, at block 730. At block 740, the value of each color component of a tuple is calculated. At block 750, the x-coordinates and the y-coordinates of the beginning point and the end point of an alignment designation bar are calculated using at least two of the four variables, A, B, C, and D. At block 760, a set of paired identification labels is generated, where the labels are of the same color as each other and an alignment designation bar is printed across the labels.

Figure 9A:
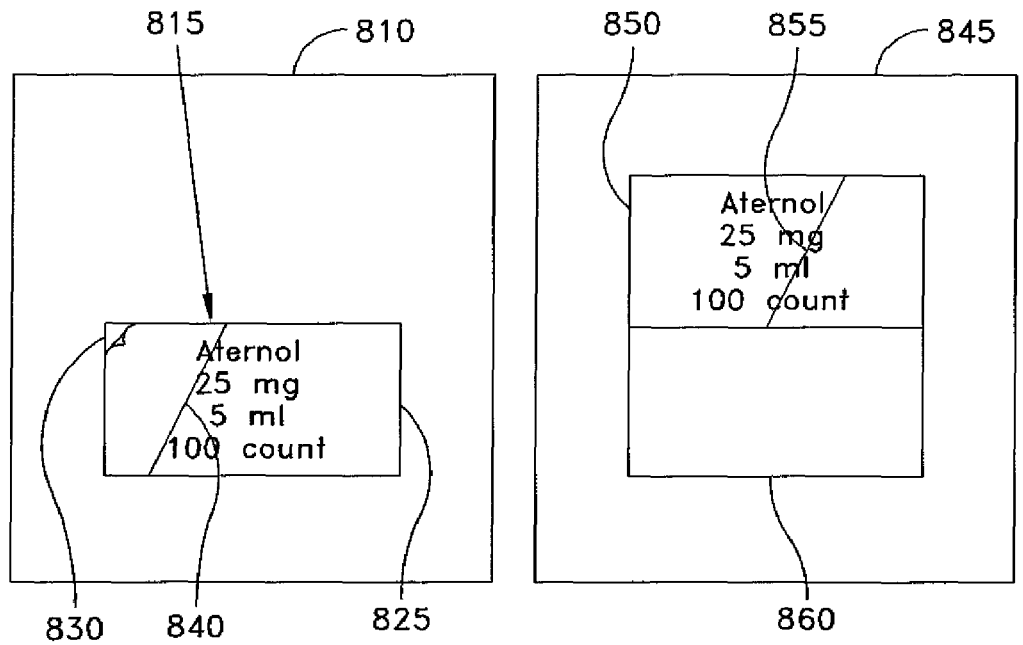
FIGS. 9A-9B illustrate an exemplary matching of a deliverable unit with an information sheet using an embodiment of the set of paired identification label.
Figure 9B:
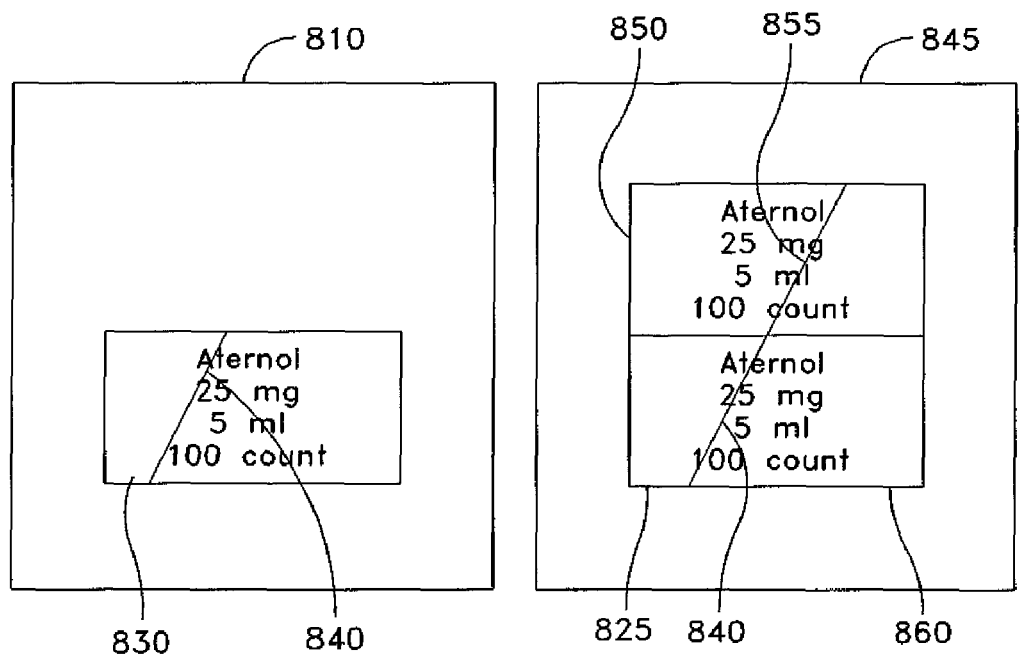

Referring now to FIGS. 9A-9B, an exemplary use of the paired identification labels according to an embodiment of the invention will be described. A set of labels 815 is affixed to a deliverable unit 810. In an exemplary embodiment, deliverable unit 810 may be a vial of medication. In an exemplary embodiment, set 815 includes two labels 825, 830. Labels 825, 830 have the same text, and the same color depending on the text. For illustrative purposes only, the text may include the name of the drug, the dose and the count of the pills or capsules in unit 810. In other embodiment, the text may be indicative of a tool in a workshop. The position of alignment designation bars 840 depend on the text of labels 825, 830. Label 830 is removably superimposed on label 825 such that label 830 may be peeled off leaving label 825 on deliverable unit 810. Label 830 has a layer of adhesive applied on the surface which is superimposed on label 825. The upper surface of label 825 may have a suitable coating to prevent permanent adhesion of the adhesive of label 830 thereon.

An information sheet 845 is generated along with a prescription for a patient. A label image 850 with an alignment designation bar 855 is generated based on the text of the prescription for the patient. As set forth above, a given prescription text will have a unique color and a unique position for alignment designation bar 855. Label image 850 would be complementary to label 825. A blank space 860 is provided below label image 850. An individual responsible for delivering deliverable unit 810 to a patient peels label 825 off unit 810 and affixes label 825 on information sheet 845. For a correct combination of deliverable unit 810 and information sheet 845, label 825 will have the same color as that of label image 850 on information sheet 845. Alignment designation bar 840 of label 825 will match alignment designation bar 855 on label image 850 previously present on information sheet 845 at the adjacent edges of label 825 and label image 850. Such a method provides three checks for ensuring dispensing of correct deliverable unit 810 to a patient with information sheet 845: (1) Label image 850 and label 825 should have the same text; (2) label image 850 and label 825 should be of the same color; and (3) alignment designation bar 855 of label image 850 should align as to position and orientation of alignment designation bar 840 of label 825 at the adjacent edges of label image 850 and label 825.

Figure 10:
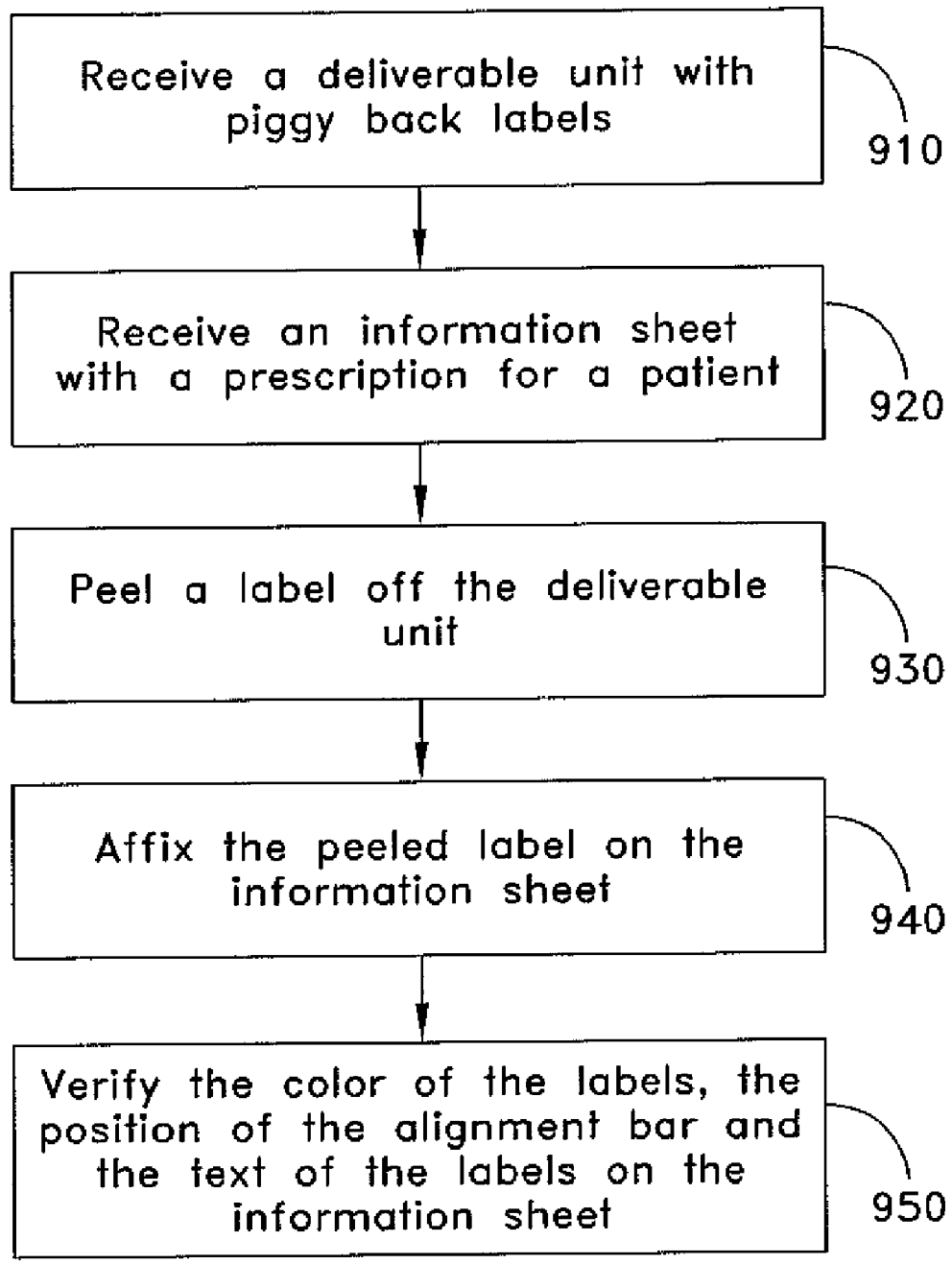
FIG. 10 illustrates a flow chart for an exemplary method for matching a deliverable unit with an information sheet.

FIG. 10 illustrates a flow chart for the method for using a set of paired identification labels described in FIG. 9. At 910, a deliverable unit with a set of paired identification labels is received. The set includes two identical labels, one removably superimposed over the other. The identical labels also include a plurality of characters indicative of the contents of the deliverable unit and at least one visual indicator. The visual indicator may include a color field, an alignment designation bar or both. An information sheet, for example, with a prescription presumably corresponding to that deliverable unit for the patient is received, at 920. The information sheet has, for example, details like the patient's name, the medication prescribed to the patient, a complementary label image including the prescription information and a blank space adjacent to the label image for receiving a complementary label. In other embodiment, the information sheet may have information pertaining to a special tool to be delivered only to authorized personnel. A label from the set of labels on the deliverable unit is peeled off the unit, at 930. At 940, the peeled label is affixed on the blank space provided on the information sheet. Three parameters are then verified: (1) the text of the label and the label image on the information sheet; (2) the color of the label and the label image on the information sheet; and (3) the position of the alignment designation bars on the label and the label image on the information sheet, at 950. If all three parameters match, then the correct deliverable unit has been paired with the correct information sheet.

In one embodiment, the set of paired identification labels or label images may have identical plurality of characters printed thereon and an alignment designation bar. In another embodiment of the invention, the set of paired identification labels may have identical plurality of characters printed thereon and be printed in same color. In yet another embodiment, the set of paired identification labels or label images may have identical plurality of characters included thereon, an alignment designation bar on each label or label image and be printed in same color.

Figures 11, 12, 13:
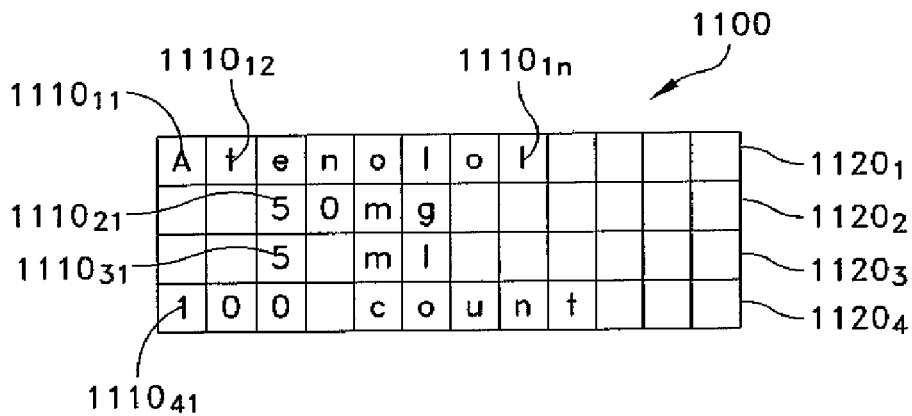
FIG. 11 illustrates text for a label 1100 with a slight difference in the characters printed thereupon as compared to label 100.
FIG. 12 illustrates an assignment of a numerical value to each character in exemplary label 1100 and calculation of row total for each row of characters in exemplary label 1100.
FIG. 13 illustrates an exemplary calculation of values of variables "A," "B," "C," and "D" based on the row totals for label 1100.

Now will be described, referring to FIG. 11, how a difference in the characters in the printed information on a label will result in a set of paired identification labels with different characteristics such as the color of the label and the position of the alignment designation bar. Label 1100 has the same information as that on label 100, except for the dosage, i.e. 50 mg instead of 25 mg. Following the same method, for exemplary label 1100, the row totals 1210, 1220, 1230, and 1240 are 174, 47, 51, and 126 for the first, second, third and fourth rows 120$_1$, 120$_2$, 120$_3$, and 120$_4$ respectively. For exemplary label 100, the values of A, B, C, and D are 174, 94, 153, and 504 respectively using the first exemplary method. For the exemplary label 100, $$A+B=174+94=268$$

$$A+C=174+153=327$$

$$A+D=174+504=678$$

For exemplary label 100, the values of R, G, and B are respectively 200 (based on the value corresponding to the last digit 8 of the sum (A+B) in the color look up table of FIG. 3), 175 (based on the value corresponding to the last digit 7 of the sum (A+C) in the color look up table of FIG. 3), and 200 (based on the value corresponding to the last digit 8 of the sum (A+D) in the color look up table of FIG. 3). Thus, the color of the generated label will be defined by the tuple (200, 175, 200).

Figure 14:
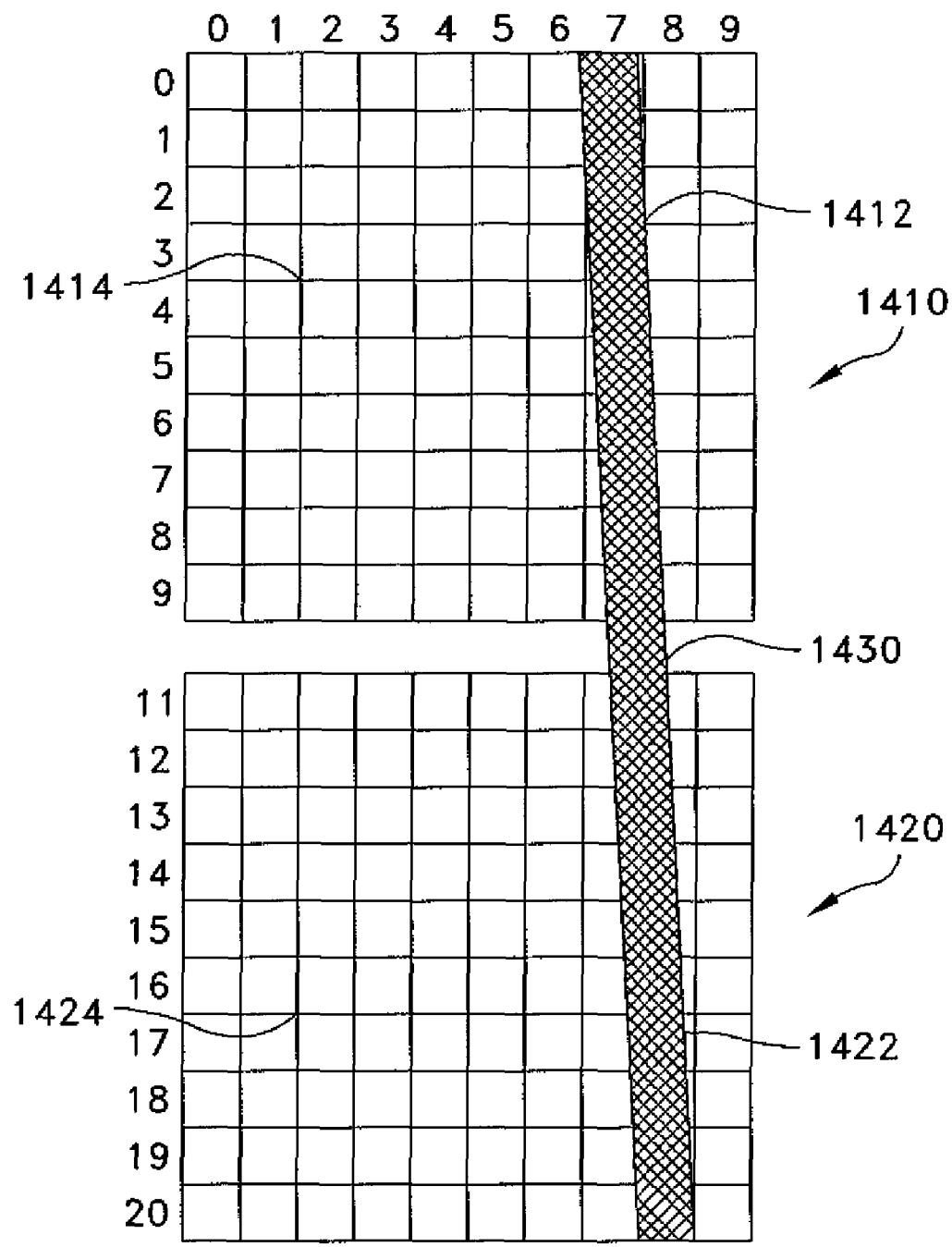
FIG. 14 illustrates the exemplary set of paired identification labels with an alignment designation bar corresponding to label 1100.

Furthermore, the x and y co-ordinates of the starting point and the end point of the alignment designation bar for label 1100 will also be different than those for label 100. In this exemplary embodiment, the y-coordinate of the beginning point of bar 1430 (of FIG. 14) is 0 and the y-coordinate of the end point of bar 1430 (of FIG. 14) is 20. In an exemplary embodiment, the x-coordinate of the beginning point of bar 1430 (of FIG. 14) is the last digit 7 of the sum (B+C=247) and the x-coordinate of the end point of bar 1430 (of FIG. 14) is the last digit 8 of the sum (B+D=598). For exemplary label 1100, the beginning point of bar 1430 (of FIG. 14) is (7, 0) and the end point of bar 1430 (of FIG. 14) is (8, 20).

Figure 15:
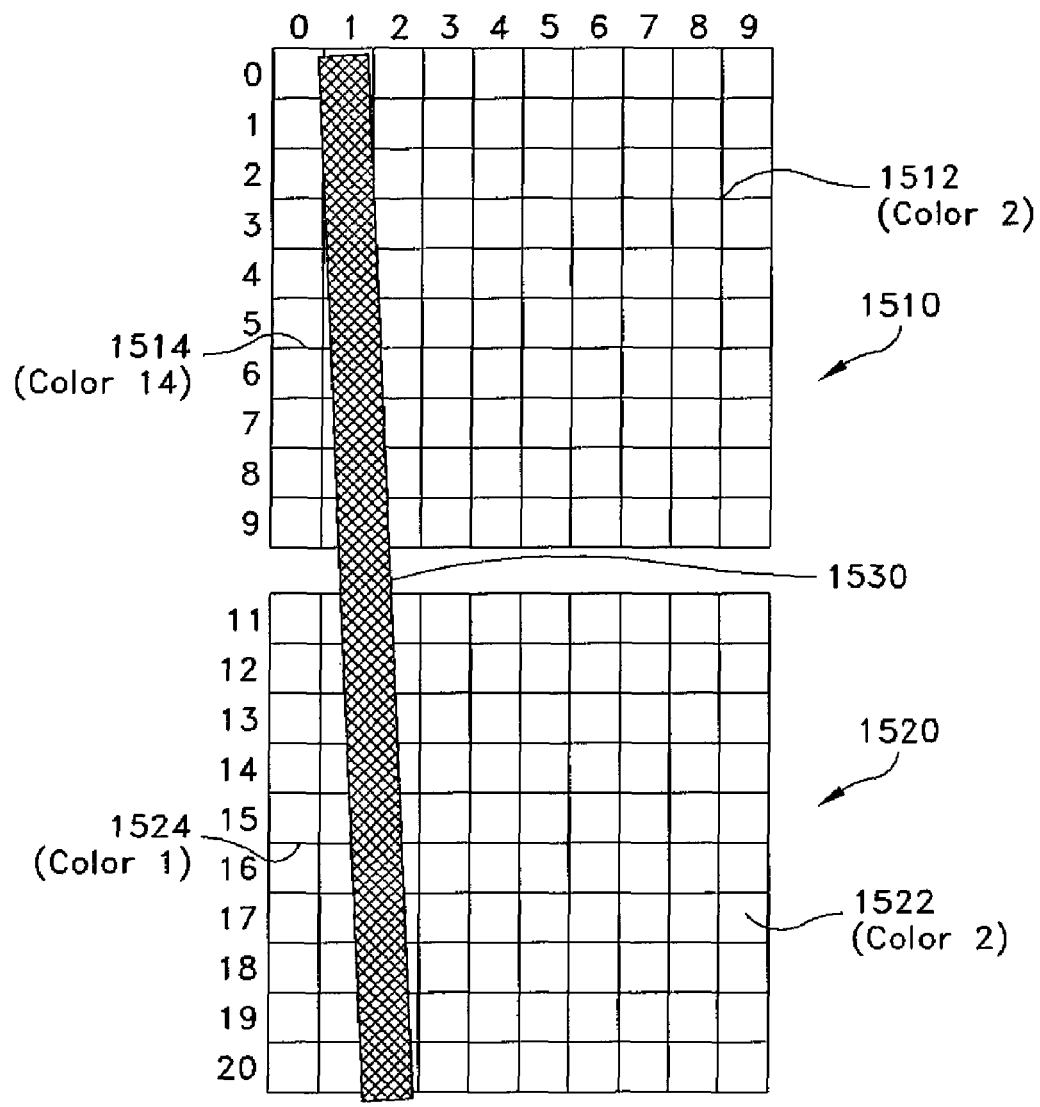
FIG. 15 illustrates another exemplary set of paired identification labels corresponding to label 100 with an alignment designation bar.

Referring now to FIG. 15 is illustrated another embodiment of a set of paired identification labels 1510, 1520, which are similar to labels 610, 620 except for one difference. Both labels 610, 620 are printed in color defined by a tuple (50, 175, 200), whereas labels 1510, 1520 use two different colors. For example, color for parts 1514, 1524 of labels 1510, 1520 respectively may be printed in a first color defined by tuple (50, 175, 200), whereas parts 1512, 1522 of labels 1510, 1520 may be printed in a second color. The second color may be determined, for example, by adding 50 to each of the components, i.e. (100, 225, 250). It will be understood that the second color may be determined in many different ways, such as subtracting instead of adding a predetermined value, or multiplying each component by a value, for example, 1.1 or 1.5. Use of two different colors on the two sides of alignment designation bar 1530 provides an additional easily verifiable parameter for ensuring that labels 1510 and 1520 belong to a single pair of identical labels.

Figure 19:
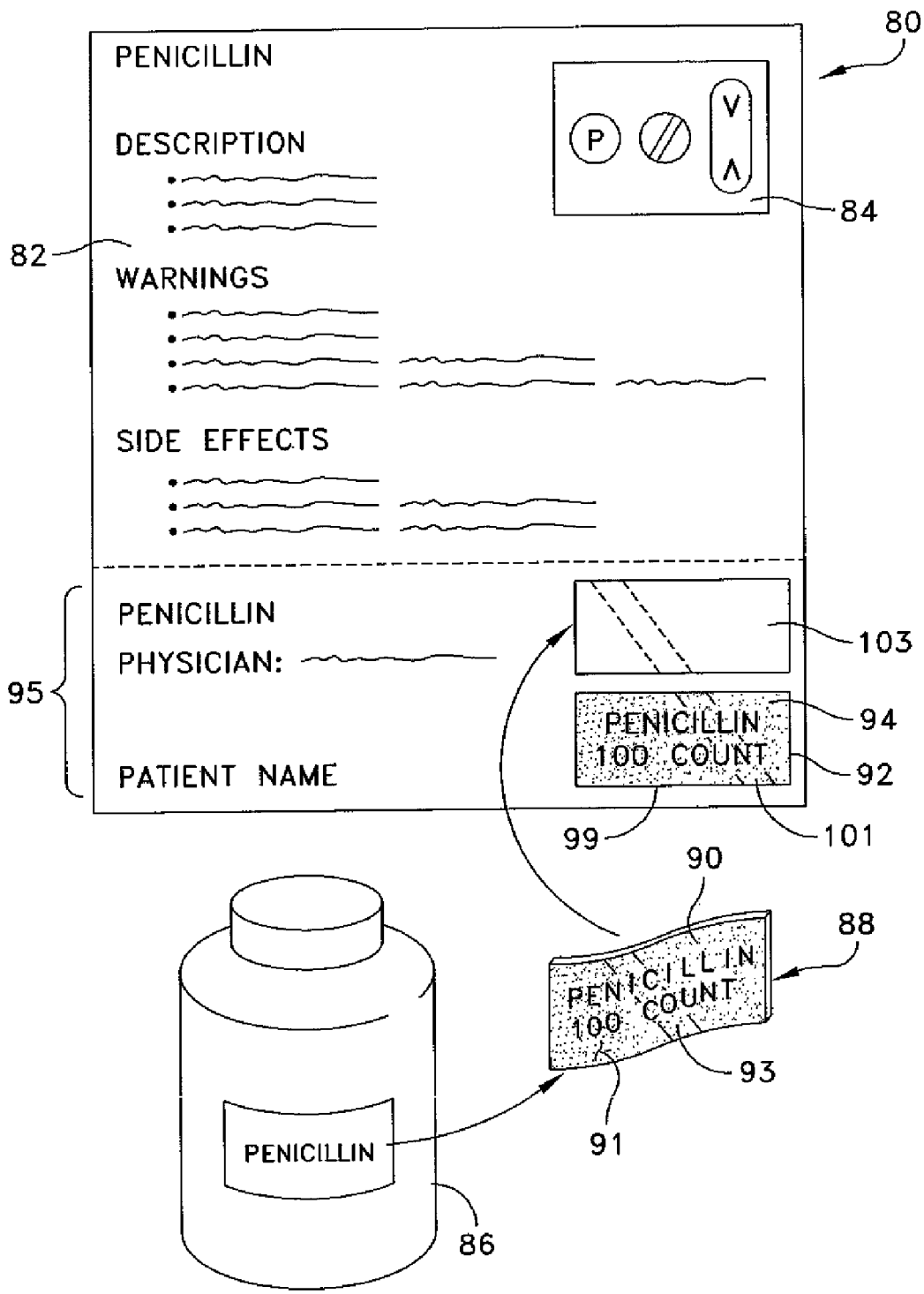
FIG. 19 illustrates an exemplary information sheet and shown with a deliverable unit with a piggy-back label.

Referring to FIG. 19, an exemplary embodiment of a printout or information sheet 80 for a pharmaceutical application is shown. The sheet 80 has an information section 82 that preferably contains some of the warnings and technical information about the pharmaceutical being conveyed. The sheet 80 also has a picture section 84 that shows color pictures of the pharmaceutical being conveyed. More than one picture may be provided if the pharmaceutical is manufactured by more than one company and comes in different sizes, shapes and/or colors.

A prepackaged pharmaceutical container or a deliverable unit 86 is also shown in FIG. 19. When such a prepackaged pharmaceutical container 86 vends from a vending machine, it contains a removable label 88. The removable label 88 identifies the pharmaceutical being in the prepackaged container 86 and also provides a code pattern or visual indicator 90 that is unique to that type of prepackaged unit-of-use. The code pattern or visual indicator 90 may be a color code, a numerical code, a graphic code or any other visual code. In the exemplary embodiment illustrated in FIG. 19, the code pattern includes a color field 91 and an alignment designation bar 93.

The printout 80 contains a tear-away section 95. A label image 92 is printed onto the tear-away section 95. The label image 92 contains a code pattern 97 that corresponds to the code pattern 90 on the removable label 88 from the prepackaged container 86. The label image 92 also contains a color field 99 and an alignment strip 101.

A label target or blank space 103 is printed adjacent to, for example, either immediately above or below the label image 92. The label target 103 shows a person where to place the removable label 88 from the prepackaged container 86.

The removable label 88 is peeled off of the prepackaged container 86 and is applied over the label target 103. Once in this position, the color field 91 of the removable label 88 should be the same color as the color field 99 of the label image 92. Furthermore, the alignment strip 93 of the removable label 88 should align with the alignment strip 101 on the label image 92.

By comparing the removable label 88 to the label image 88, two goals are achieved. First, by checking if the code pattern 90, 97 match, it can be seen that the proper prepackaged pharmaceutical container 86 was vended from the vending machine. This safeguards against any human error that may have occurred during the filling of the vending machine. Second, the tear-away section 95 of the printout 80 is removed and kept by the office staff, thereby providing a permanent record of what was vended from the vending machine.

Figures 21, 22:
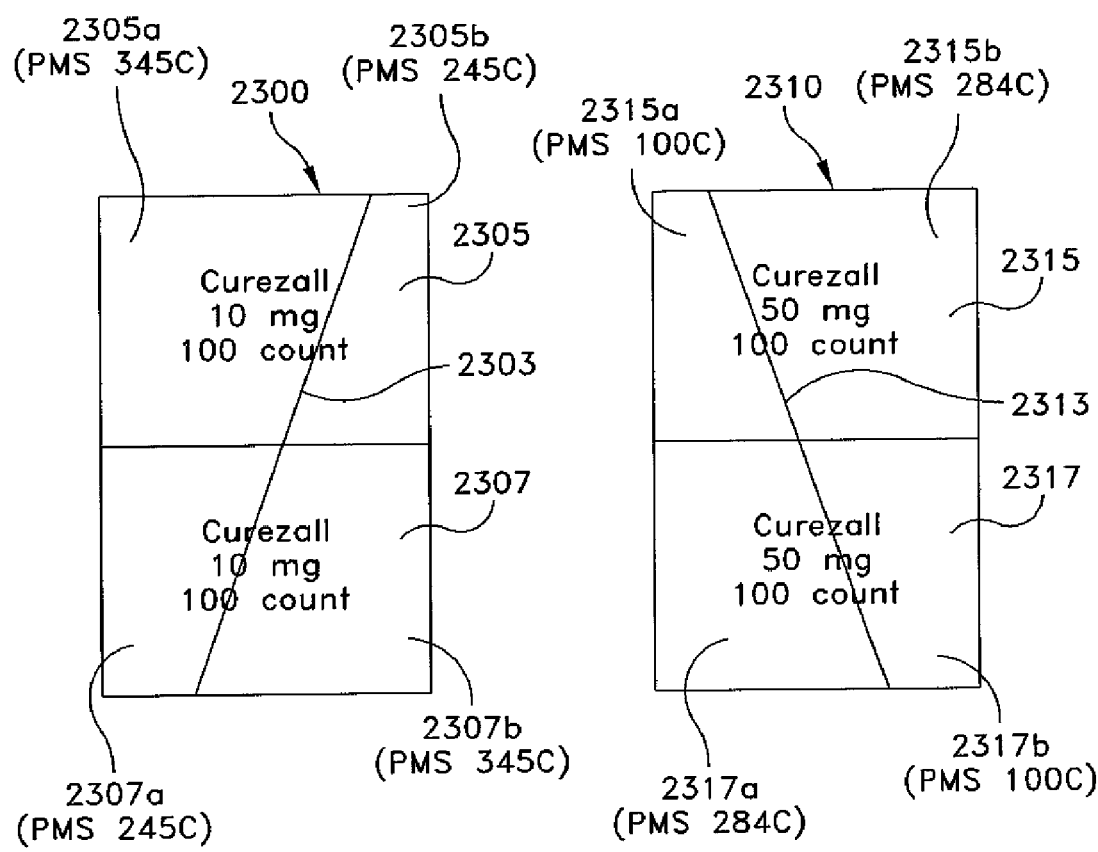
FIG. 21 illustrates an exemplary conversion table for RGB and Pantone Matching System (PMS) Colors.
FIG. 22 illustrates another embodiment of paired identification labels using two PMS colors.

In yet another embodiment, a set of paired identification labels may be created using a different color system such as Pantone Color Matching System (PMS) published by Pantone, Inc., 590 Commerce Boulevard, Carlstadt, N.J. 07072. Other color systems such as Natural Color System published by Scandinavian Colour Institute, Stockholm, Sweden and Munsell Color system may also be used. FIG. 22 illustrates a partial table listing corresponding PMS colors for a few colors defined in RGB system. One of ordinary skill in the art can modify the color look up process to either derive a PMS color from the RGB color or may directly establish a color look up table to determine a PMS color based on the plurality of characters contained in a label. Hence, such a process is not described in detail for the sake of brevity. As per the illustrated embodiment, a set includes a limited number of predetermined colors. The colors for the labels are selected only this limited set.

Referring now to FIG. 22, there are illustrated two sets of paired identification labels 2300, 2310. Set 2300 includes two labels 2305, 2307 and set 2310 includes two labels 2315, 2317. An alignment designation bar 2303 divides label 2305 into two parts 2305a, 2305b and label 2307 into two parts 2307a, 2307b. Similarly, an alignment designation bar 2313 divides label 2315 in two parts 2315a, 2315b and label 2317 into two parts 2317a, 2317b. Parts 2305a and 2307a are adjacent to each other and parts 2305b and 2307b are adjacent to each other. In the illustrated example, label set 2300 for ten (10) milligrams (mg) dosage uses colors PMS 345C and PMS 245C. Parts 2305a and 2307b are generated in color PMS 345C whereas parts 2305b and 2307b are generated in color PMS 245C. Label set 2310 for fifty (50) mg dosage, on the other hand, uses colors PMS 100C and 284C. Particularly, parts 2315a and 2317b are generated in color PMS 100C, whereas parts 2315b and 2317a are generated in color PMS 284C. Thus, adjacent parts 2305a and 2307a are printed in different colors and similarly, 2305b and 2307b are printed in different colors. By using two colors for each set of paired identification labels, thirty (30) different combinations are available from the list of six (6) PMS colors in the table of FIG. 22.

In an exemplary embodiment, using, for example, the character look up table 2300 of FIG. 23, the two colors may be calculated as follows:

$A$=Row 1 Total $B$=Row 2 Total $C$=Row 3 Total $D$=Row 4 Total

Color 1=$(B*5)+(C*101)+(D*109)$; and

Color 2=$(B*367)+(C*11)+(D*7)$

The digits of each calculated values are added until a single digit remains. Then the color may be determined using, for example, the color look up table 300 of FIG. 4. If a resulting sum is "10", zero is used to look up a color value from table 300 of FIG. 4.

Figure 20A:
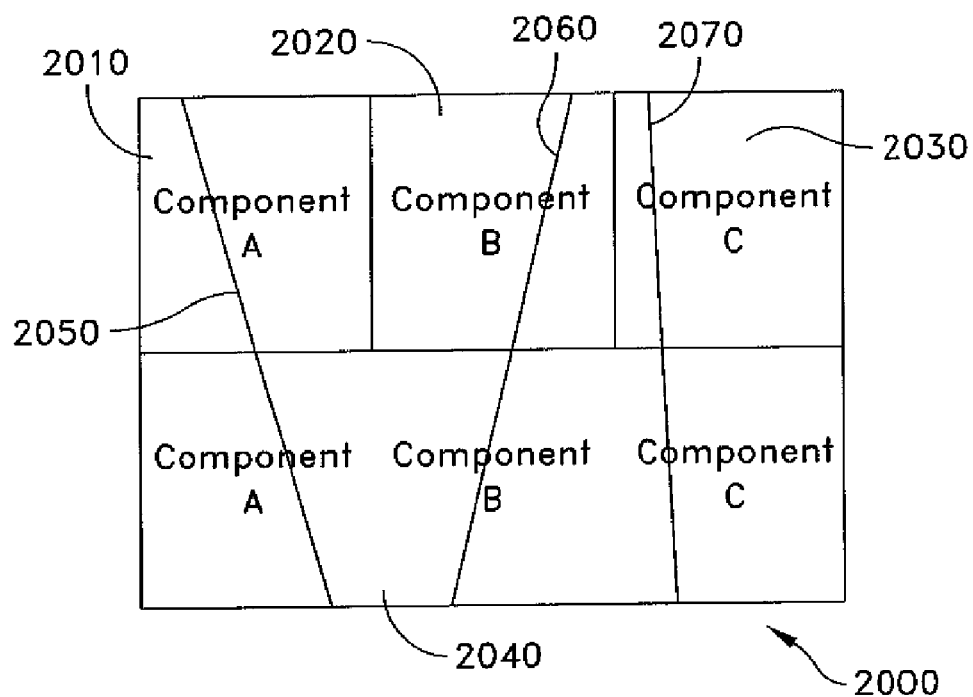
FIGS. 20A-20B illustrate two exemplary sets of labels wherein a plurality of labels are combinedly paired with at least one other label or label image.

Referring now to FIG. 20A, another embodiment 2000 of paired identification labels and/or label image is illustrated. A plurality of labels 2010, 2020, 2030 is matched with a label image 2040. Labels 2010, 2020, 2030 are matched with one another. The visual indications to match labels 2010, 2020, 2030, with label image 2040 included alignment designation bars 2050, 2060, 2070. The embodiment of FIG. 20 may be used to match a plurality of deliverable units with a single information sheet. For example, label 2010 may be affixed on a vial of a vaccine protein and label 2020 may be affixed on a vial of diluent which needs to be combined with the vaccine protein before the vaccine is delivered to a patient. Each instance of a visual indicator on label image 2040 is associated with a distinct label on a deliverable unit. Such a plurality of visual indicators thus reminds an individual responsible that more than one deliverable unit are to be associated with such an information sheet and ensures that the correct number and type of deliverable units are ultimately delivered.

Figure 20B:
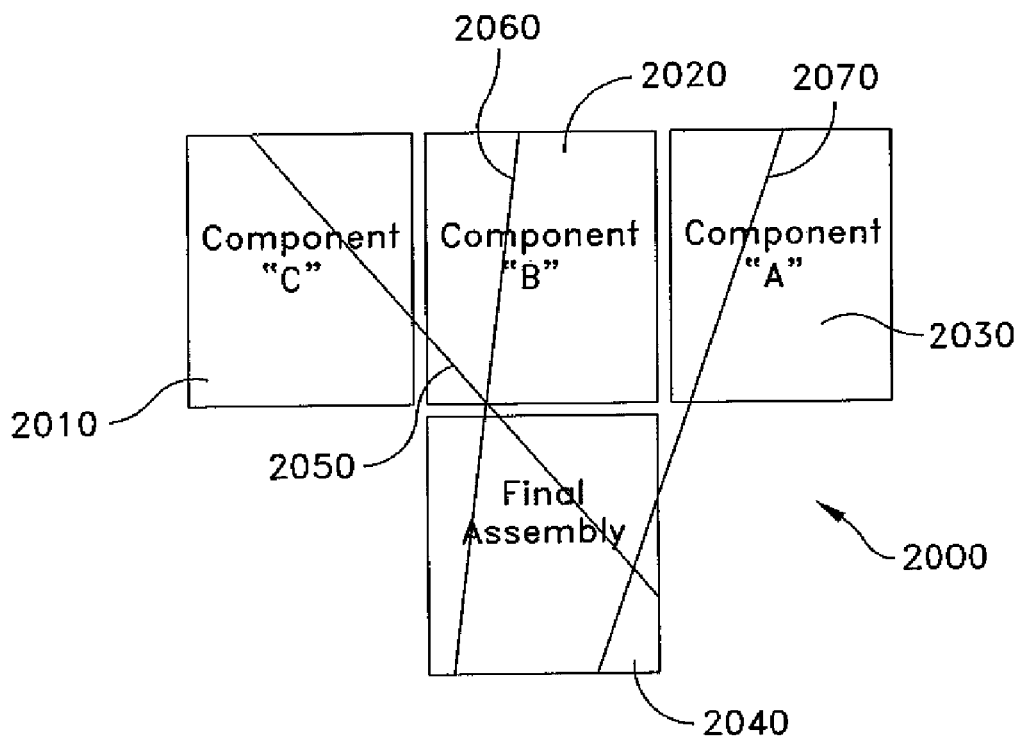
Figure 20C:
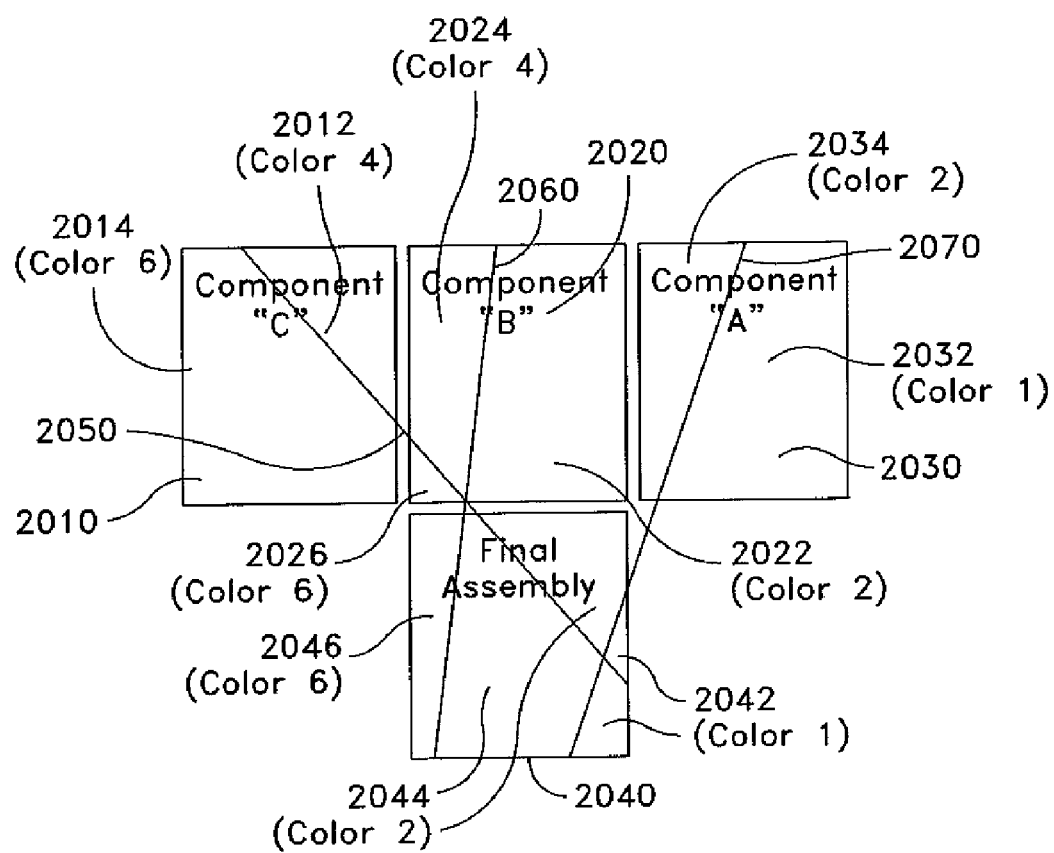
FIG. 20C illustrates the method of determining different colors for the set of labels illustrated in FIG. 20B.

FIG. 20B illustrates another embodiment of the paired set of identification labels. In the illustrated embodiment, labels 2010, 2020, and 2030 are matched and/or aligned with one another and combinedly with a label image 2040. The starting and end points of alignment designation bars 2050, 2060. 2070 may be calculated by summing up the digital values associated with text contained in all three (3) labels 2010, 2020, 2030. One of ordinary skill in the art can derive algorithms for determining positions of bars 2050, 2060, 2070, based on the—methods previously discussed in the present application, e.g., taking values based on text and numerals on labels to determine bar endpoints. Referring to FIG. 20C, there will be described a method of determining the colors as visual indicators for the embodiment having a plurality of labels matched or aligned with a label image. In an exemplary embodiment, the two (2) colors (Color 1, Color 2) for label 2030 are determined in a fashion similar to that for the label set illustrated in FIG. 22 and described in the associated description, using the text of label 2030. In the illustrated embodiment, label 2030 is divided into two portions 2032, 2034 by alignment designation bar 2070. Portion 2032 is on right side of bar 2070 and is printed in Color 1 while portion 2034 is on left side of bar 2070 and is printed in Color 2. Label 2020 is divided into three (3) portions 2022, 2024, 2026 by alignment designation bars 2050, 2050. Two (2) colors (Color 3, Color 4) for label 2020 are also determined in fashion similar to those for label 2010. However, portion 2022, which is adjacent to portion 2034, is printed in Color 2, disregarding the color (Color 3) determined based on the text of label 2020. Portion 2024 is printed in Color 4. Similarly, two (2) colors (Color 5, Color 6) for label 2010 are determined based on the text of label 2010. However, portion 2012, which is adjacent to portion 2024, is printed in Color 3, disregarding the color (Color 5). Portion 2014, on other hand, is printed in Color 6 as determined above. Portion 2026, which is adjacent to portion 2014, of label 2020 is also printed in Color 6.

Label image 2040 is divided into three (3) portions 2042, 2044, 2046 by alignment designation bars 2060, 2070. Portion 2042 which is on right side of bar 2070 is printed in Color 1. Portion 2044 between bars 2060, 2070 is printed in Color 2 and portion 2046 on the left side of bar 2060 is printed in Color 6. Thus, when labels 2010, 2020, 2030 are correctly matched with label image 2040, adjacent portions, which are printed in the same color, match with each other, and provide a visual check that the intended components have been correctly assembled and dispensed together. Even a slight change in the text of any of labels 2010, 2020, 2030 will result in a different color and create a discrepancy with the colors on label image 2040.

It will be apparent to those skilled in the art that modifications and variations may be made in the method and the system of the present invention without departing from the spirit or scope of the invention. It is intended that the present invention cover the modification and variations of this invention provided they come within the scope of the appended claims and their equivalents.

What is claimed is:

1. A method for matching a deliverable unit with an information sheet using a set of paired identification labels, said method comprising the steps of:
    affixing a set of identification labels on the deliverable unit, said set generated based on a plurality of characters included thereon, said plurality of characters being indicative of the content of the deliverable unit, said set comprising:
        a first label having said plurality of characters included thereon;
        a first visual indicator printed adjacent to at least one edge of said first label;
        a second label in having said plurality of characters included thereon;
        a second visual indicator printed adjacent to at least one edge of said second label, said second label being identical to said first label, wherein said second label is removably superimposed on said first label;
    generating an information sheet, said information sheet further comprising:
        a label image complementary to said first label, and wherein said label image has a third visual indicator printed adjacent to at least one edge of said label image, wherein said third visual indicator is adapted to align or match with said second visual indicator; and
        a blank space adjacent to said label image;
    removing said second label from said deliverable unit; and
    affixing said second label in said blank space adjacent to said label image,
    wherein said second label and said label image are printed in the first color,
    wherein said second and third visual indicators align or match with each other at adjacent edges of said second label and said label image, and
    wherein said second label and said label image have printed thereon the plurality of characters, wherein the plurality of characters are indicative of content in the deliverable unit and indicative of a content to be delivered to a bearer of said information sheet.

2. The method of claim 1, wherein said visual indicator comprises a first color, said first color generated based on the plurality of characters.

3. The method of claim 1, wherein said visual indicator comprises an alignment designation bar, the attributes of said alignment designation bar being based on the plurality of characters.

4. The method of claim 1, wherein said visual indicator comprises:
    a first color, said first color generated based on the plurality of characters; and
    an alignment designation bar, the attributes of said alignment designation bar being based on the plurality of characters.

5. The method of claim 1, wherein said second label has a coating of adhesive on the surface to be affixed to said blank space.

6. The method of claim 1, wherein said first label has a coating on the surface whereon said plurality of characters are included, said coating capable of preventing permanent adhesion of said second label to said first label.

7. The method of claim 1, wherein a plurality of deliverable units are matched with said information sheet, wherein each of said plurality of deliverable units comprises a set of identification labels, wherein each of said sets comprises a removably affixed label, wherein each of said removably affixed label comprises a visual indicator, adapted to align or match with a visual indicator on said label image on the information sheet.

8. A set of paired identification labels comprising:
    a first label having a plurality of characters printed thereon;
    a first alignment designation bar printed across said first label;
    a second label having said plurality of characters printed thereon; and
    a second alignment designation bar printed across said second label;
wherein when said first and second labels are located adjacent to each other, said first and second alignment designation bars align with each other at the edges of said first and second labels.

9. The set of paired identification labels of claim 8, wherein said first and second labels are printed in a first color.

10. The set of paired identification labels of claim 8, wherein said first alignment designation bar divides said first label into first and second parts,
    wherein said second alignment designation bar divides said second label into third and fourth parts,
    wherein said first and third parts are printed in a first color; and
    wherein said second and fourth parts are printed in a second color.

11. The set of paired identification labels of claim 10, wherein said first and third parts are adjacent to each other and said second and fourth parts are adjacent to each other.

* * * * *